US012478407B1

(12) United States Patent
Işin et al.

(10) Patent No.: US 12,478,407 B1
(45) **Date of Patent: *Nov. 25, 2025**

(54) ADJUSTABLE EXTERNAL FIXATOR AND FIXATOR KIT FOR ANGLE CORRECTION OF A BONE

(71) Applicants: Şehmuz Işin, Istanbul (TR); Baran Işin, Istanbul (TR); Ikbal Işin, Istanbul (TR)

(72) Inventors: Şehmuz Işin, Istanbul (TR); Baran Işin, Istanbul (TR); Ikbal Işin, Istanbul (TR)

( * ) Notice: Subject to any disclaimer, the term of this patent is extended or adjusted under 35 U.S.C. 154(b) by 0 days.

This patent is subject to a terminal disclaimer.

(21) Appl. No.: 19/223,637

(22) Filed: May 30, 2025

Related U.S. Application Data

(63) Continuation of application No. 18/812,512, filed on Aug. 22, 2024, now Pat. No. 12,318,118.

(51) Int. Cl.

| | |
|---|---|
| ***A61B 17/60*** | (2006.01) |
| ***A61B 17/64*** | (2006.01) |
| ***A61B 17/66*** | (2006.01) |
| *A61B 17/56* | (2006.01) |

(52) U.S. Cl.
CPC .......... *A61B 17/66* (2013.01); *A61B 17/6416* (2013.01); *A61B 2017/564* (2013.01)

(58) Field of Classification Search
CPC ................ A61B 17/66; A61B 17/6416; A61B 2017/564
USPC .. 606/54, 57, 58, 59, 278, 280, 70, 71, 282, 606/87, 89, 102, 105
See application file for complete search history.

(56) References Cited

U.S. PATENT DOCUMENTS

| | | | | |
|---|---|---|---|---|
| 4,696,293 | A | 9/1987 | Ciullo | |
| 5,468,241 | A | 11/1995 | Metz-Stavenhagen et al. | |
| 5,490,851 | A | 2/1996 | Nenov et al. | |
| 5,971,984 | A | 10/1999 | Taylor et al. | |
| 7,892,258 | B2 | 2/2011 | Iott et al. | |
| 9,095,380 | B2 | 8/2015 | Mir et al. | |
| 12,318,118 | B1 * | 6/2025 | Işin .................... | A61B 17/6416 |
| 2002/0164905 | A1 | 11/2002 | Bryant | |
| 2003/0105460 | A1 | 6/2003 | Crandall et al. | |
| 2003/0191475 | A1 | 10/2003 | McGuire | |
| 2012/0143191 | A1 | 6/2012 | Foote | |
| 2023/0142859 | A1 | 5/2023 | Schafer et al. | |
| 2023/0363801 | A1 | 11/2023 | Zhang et al. | |

FOREIGN PATENT DOCUMENTS

| | | | |
|---|---|---|---|
| WO | 2009007009 | A1 | 1/2009 |

* cited by examiner

*Primary Examiner* — Eduardo C Robert
*Assistant Examiner* — David C Comstock
(74) *Attorney, Agent, or Firm* — Hayes Soloway, PC

(57) ABSTRACT

An adjustable external fixator and fixator kit for angle correction on a bone comprising a head element, arm, shaft element, and adjustable distraction element. Sizing inserts of different discrete sizes are provided and are installable between ends of the head element and ends of the arm. When installed, the fixator can fit patients of any size. The sizing inserts can be blocks or rails secured by threaded fasteners. The fixator and kit may also comprise a wrench releasably secured to the shaft element can be used to adjust a length of the distraction element. The fixator and kit may also comprise an angle measurement tool to measure angle of distraction.

20 Claims, 7 Drawing Sheets

ADJUSTABLE EXTERNAL FIXATOR AND FIXATOR KIT FOR ANGLE CORRECTION OF A BONE

CROSS-REFERENCE TO RELATED APPLICATIONS AND PRIORITY

This patent application is a Continuation of U.S. patent application Ser. No. 18/812,512 filed Aug. 22, 2024, issued as U.S. Pat. No. 12,318,118 on Jun. 3, 2025. This patent application is herein incorporated by reference in its entirety.

BACKGROUND OF THE INVENTION

1. Field of the Invention

The invention is in the field of surgical instruments or methods for treatment of bones or joints, in particular alignment, compression, or distraction mechanisms.

2. Description of the Related Art

Predispositions or accident-related misalignments in the area of the tibial (shinbone) head can lead to one-sided overloading and thus to premature arthrosis of the knee joint. An established treatment procedure is the correction of the leg axis with the aim of preventing damage to the overloaded cartilage or relieving the already damages cartilage. If the center of the misalignment is located close to the knee joint, as is very often the case, the correction center must also be chosen close to the knee joint.

A common procedure is to surgically cut the tibial head and stabilize it with a plate after correcting the axis. While the very common corrections in the direction of valgus (knock-knees) are less likely to cause complications, corrections in the direction of varus (bow-knees) carry a considerable risk of complications. The cause is the peroneal nerve, which, due to evolutionary reasons, runs laterally around the head of the fibula before it enters the ventral muscle group. In the case of an acute correction in the direction of varus and stabilization with an osteosynthesis plate, the already tense nerve experiences an additional acute lengthening, which can lead to temporary or permanent failures and thus to sensory disturbances and/or loss of function (foot drop).

The axis correction in both the varus and valgus directions can be achieved by closing the correction angle after removing a bone wedge (closed wedge) or by opening the correction angle (open wedge). With a closed wedge correction, the leg becomes slightly shorter, but the advantage is the direct bone contact, which accelerates healing. With an open wedge correction, the leg becomes slightly longer, with larger opening angles, spongiosa (soft bone substance) frequently has to be used, for example can be introduced from the basin comb so as to result in an osseous bridging, which significantly expands the engagement. In both cases, the size of the correction angle must be precisely calculated beforehand, since subsequent corrections are not possible without another operation. Another disadvantage of plate osteosynthesis, regardless of whether the correction is in the direction of varus or valgus, is the need to remove the implant again, since it is not uncommon for previously damaged knee joints to later require a prosthetic surface replacement, so that the implants are then in the way. A follow-up operation to remove the metal after the bone has healed is therefore the rule.

One improvement to this method is described in WO 2009/007009 A1 by Baumgart, which is not admitted to being prior art by its description in this Background section. Baumgart discloses an external fixator for correcting the angle of a bone, in particular of the tibial head, which has an elongated head element. The head element has a receiving opening at each of its ends. At one end a laterally projecting boom is provided with a bore at the end, and at its other end a holding flange protruding on the same side as the boom. An elongated shaft element is provided, which has a receiving opening at each of its ends, and at one end has an arm which is inclined away from the shaft element such that it forms an angle of 110° to 160°, preferably 120° to 130°, with it, and which has a bore at the end. Between its ends on the side opposite the arm has a further holding flange, a screw thread inserted into the bores in the arm, or a hinge screw that can be used to form a hinge joint and has a continuous central guide channel. Fastening elements, each held in clamping devices of a receiving opening and fixable on the bone side, as well as a distraction element, e.g. a threaded spindle, which is hinged at each end to a holding flange is also provided.

There are several problems with the Baumgart apparatus. A hospital must keep a large number of Baumgart fixators in inventory to accommodate patients of different sizes. For example, they must be provided in sizes small, medium, and large, or even a greater number of sizes. This leads to a financial load on the medical facility and a burden to track every version of the fixator. The absence of an apparatus size needed for a particular patient could lead to surgery cancellation, postponement, or an attempt to use a wrong sized fixator during a surgery. The requirement for a quantity of differently sized products leads to an inefficient use of human resources, raw materials, warehousing, logistics, and transportation.

Another problem with the Baumgart apparatus is that a surgeon cannot tell whether an osteotomy (bone cut for bone angulation) is complete. Incomplete osteotomies cause patient pain due to connected bones and causing small cracks during the distraction. The Baumgart fixator prevents a surgeon from discerning whether the osteotomy is complete when the fixator is installed.

Yet another problem is that the Baumgart apparatus prevents angulation from being measured and corrected in situ. The angle must be checked using x-ray imaging.

What is needed, therefore, is an external fixator that does not have the disadvantages described above. An improved external fixator does not require a large inventory of different fixator sizes, permits a surgeon to determine whether an osteotomy is complete, permits angulation to measured and corrected, and can be provided as kit with differently sized selectable inserts.

SUMMARY OF THE INVENTION

The present invention is modularly adjustable external fixator for angle correction of a bone that satisfied these needs. The fixator comprises a head element having a head element sizing insert for adjusting the length of the head element, a shaft element comprising an arm and an arm sizing insert for adjusting the length of the arm, and a length adjustable distraction element, whereby a size of the head element sizing insert and a size of the arm sizing insert can be selected to produce a predetermined external fixator configuration that corrects an angle of a bone. The fixator can be provided as a kit with inserts of different sizes to permit the assembled fixator to fit differently sized patients.

These and other benefits, features, and advantages will be made clearer in the accompanying description, claims, and drawings.

BRIEF DESCRIPTION OF DRAWINGS

The novel features believed characteristic of the advantageous embodiments are set forth in the appended claims. The advantageous embodiments, however, as well as a preferred mode of use, further objectives, and advantages thereof, will best be understood by reference to the following detailed description of an advantageous embodiment of the present disclosure when read in conjunction with the accompanying drawings, wherein:

DETAILED DESCRIPTION OF THE INVENTION

Figure 1:
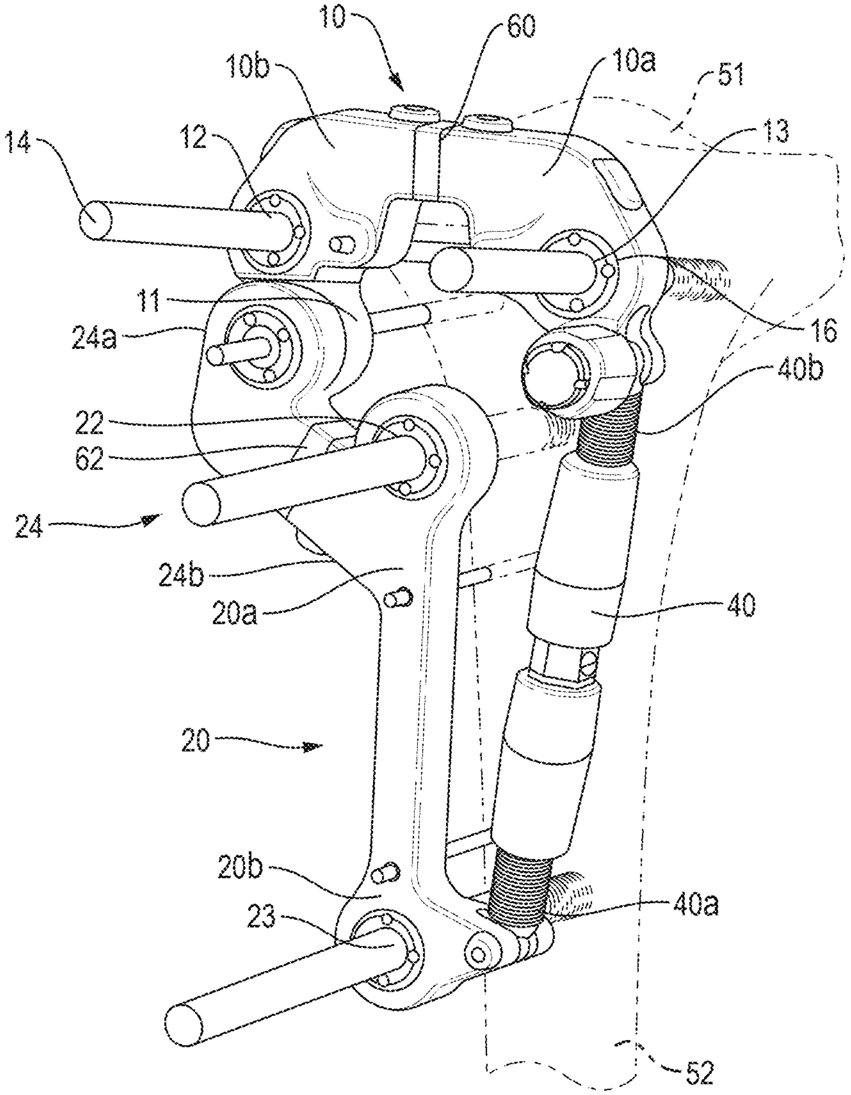
FIG. 1 is an orthogonal view of a fixator according to the present invention in which the sizing inserts are blocks without rails.

A modular, adjustable external fixator for correcting an angle of a bone according to the present invention is shown in FIGS. 1-6. Turning to FIG. 1, the fixator comprises an elongated head element 10, an elongated shaft element 20, and a length-adjustable distraction element 40. The head element comprises a head element first end 10*a*, a head element second end 10*b* opposite the head element first end, a straight head element sizing insert 60, and a projecting arm 11 extending from the head element second end 10*b*. The head element sizing insert 60 must be straight instead of angled or curved in order to maximize strength and to accurately calculate distraction angles.

The straight head element sizing insert 60 is configured to be secured between the head element first end 10*a* and the head element second end 10*b* to adjust a length of the head element.

The elongated shaft element 20 comprises a shaft element first end 20*a*, an elongated arm 24 inclined away from the shaft element first end 20*a*, and a shaft element second end 20*b* opposite the shaft element first end. The elongated arm 24 comprises an arm first end 24*a* configured to be rotatably attached to the projecting arm 11, and an arm second end 24*b* opposite the arm first end attached to the shaft element first end 20*a*. The elongated arm 24 further comprises a straight arm sizing insert 62 configured to be secured between the arm first end and the arm second end. The arm sizing insert 62, like the head element sizing insert 60, must also be straight instead of angled or curved in order to maximize strength and to accurately calculate distraction angles.

The length-adjustable distraction element 40 comprises a distraction element first end 40*a* configured to be rotatably attached to the shaft element second end 20*b* and a distraction element second end 40*b* configured to be rotatably attached to the head element first end 10*a*.

In FIG. 1, the sizing inserts 60 and 62 are shown as square blocks. The blocks could also be rectangular, semi-round, semi-circular, or other shapes. A size of the head element sizing insert 60 and a size of the arm sizing insert 62 is selected to produce a predetermined external fixator configuration that corrects an angle of a bone. Examples of bone areas that are appropriate for use with this external fixator include, but are not limited to, the tibial plateau, femoral condyle, and distal tibia.

The fixator also comprises a first receiving opening 13, a second receiving opening 12, a third receiving opening 22, and a fourth receiving opening 23. Each opening has a clamp 16 associated therewith. In use, a surgeon places bone screws 14 into the bone through respective receiving openings and removably secures them with respective clamps 16. In this way, fixation is achieved.

The fixator size is adjusted by selecting sizing inserts of a particular size to produce the desired bone configuration. The length of the head element 10 is adjusted by selecting one from a selection of sizing inserts 60 of discrete sizes, which adjusts the distance between the upper two bone screws 14 shown in FIG. 1. A proper sizing insert is selected by a surgeon from the plurality of discrete sizes to adjust a size of the fixator to any patient. In particular, the sizing element will result in a head element 10 length that when assembled is suitable for patients having proximal tibial mediolateral widths (tML) between 60 mm and 90 mm, which covers substantially all patients, including various anatomies and ethnicities.

The orientation between the diaphyseal bone screws, shown as the lower two bone screws 14 in FIG. 1, is adjusted by selecting one from a selection of sizing inserts 62 of discrete sizes. The sizing inserts also keep the fixator components stable rotationally. The sizing inserts 60 and 62 can be provided in sizes extra small, small, medium, large, and extra-large relative to each other, which corresponds to differently sized patients. Five different sizes cover all patient sizes, but more or fewer than five could be provided.

Figure 2:
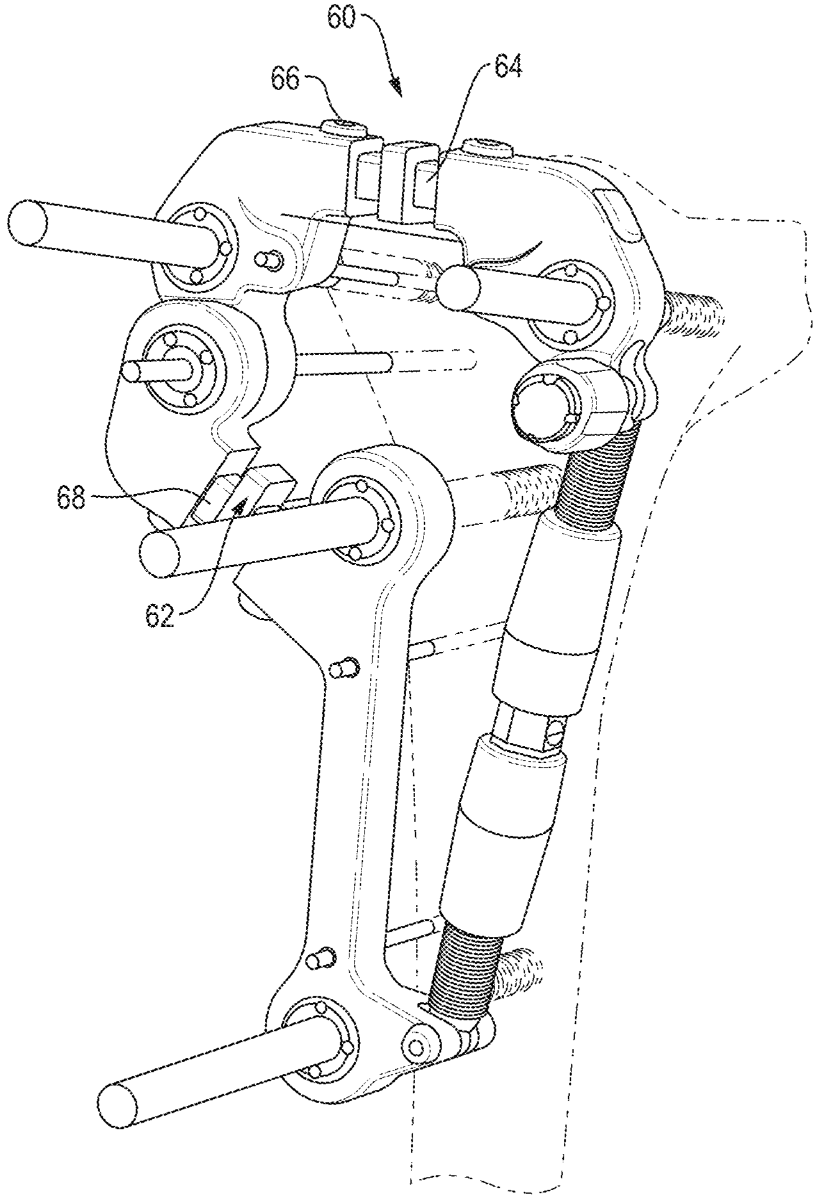
FIG. 2 is an orthogonal view of a fixator according to the present invention in which the sizing inserts are rails with blocks.

In FIG. 2, the sizing inserts 60 and 62 comprise rails 64 and 68 respectively instead of only blocks. The head element first end 10*a* and head element second end 10*b* have lateral or axial holes sized to receive the head element rail 64. The head element first end 10*a* and head element second end 10*b* also have radial holes sized to receive threaded fasteners 66. The threaded fasteners can include screws, such as set screws, or bolts. After the rail 64 is inserted in the holes in the head element first and second ends, the length is adjusted to a desired length. Then the threaded fasteners 66 are installed to fix the length of the head element 10 to the desired length.

Likewise, the arm first end 24*a* and arm second end 24*b* have lateral or axial holes sized to receive the arm element rail 68. The arm first end 24*a* and arm second end 24*b* may also have radial holes sized to receive threaded fasteners 66. After the rail 68 is inserted in the holes in the arm first and second ends, the length is adjusted to a desired length. Then the threaded fasteners 66 are installed to fix the length of the arm 24 to the desired length.

Figure 3:
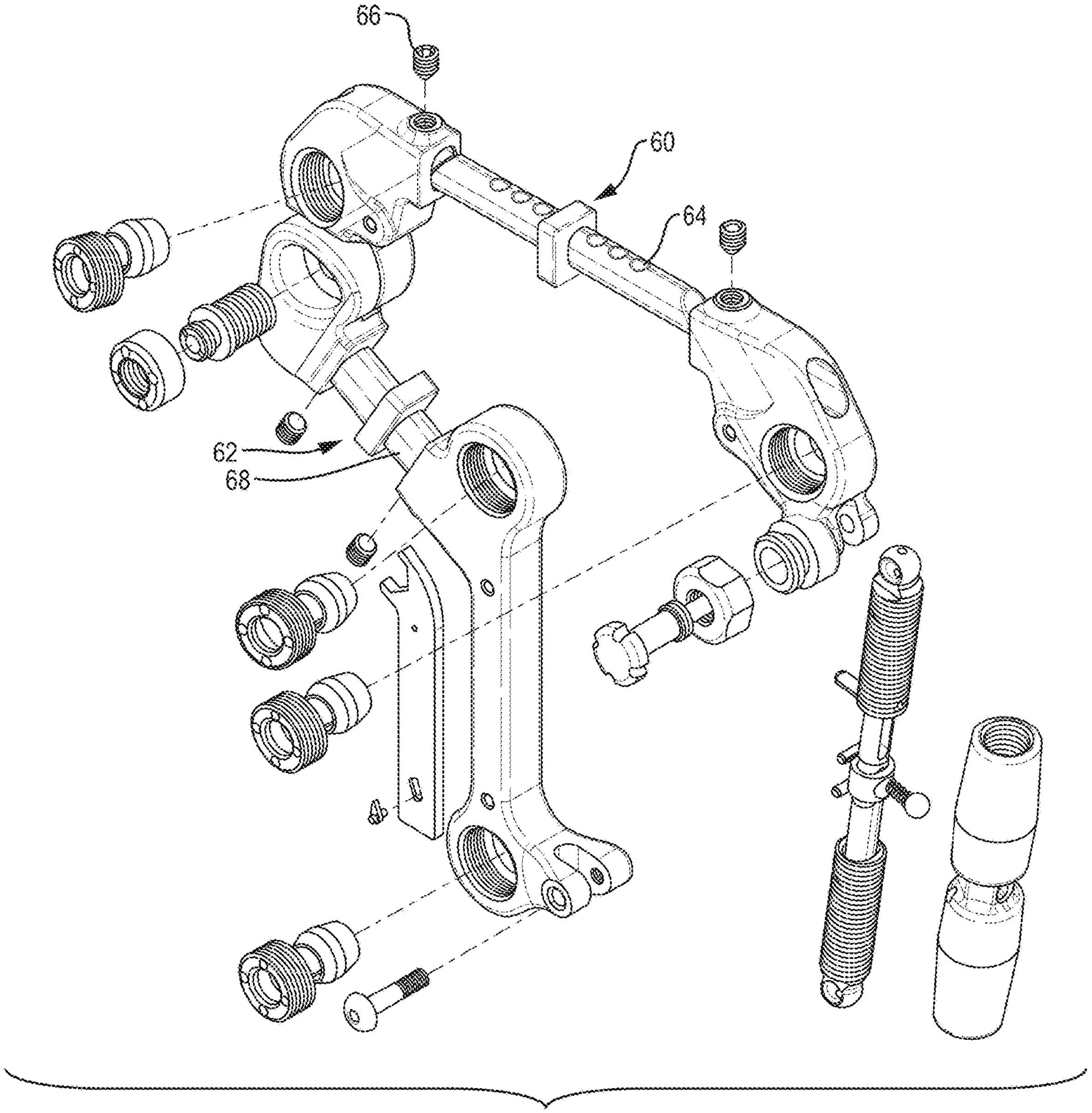
FIG. 3 is an exploded view of the fixator of FIG. 2 showing additional details of the sizing insert rail assemblies.

FIG. 3 is an exploded view of the fixator of FIG. 2 showing additional details of the sizing insert rail assemblies, threaded fasteners, clamps, and openings. Note that the head element rail 64 can be provided with a plurality of indentations or holes shown in this figure that facilitate fixing the length of the head element 10 with the threaded fasteners 66. The arm element rail 68 may also have indentations or holes.

Figure 4:
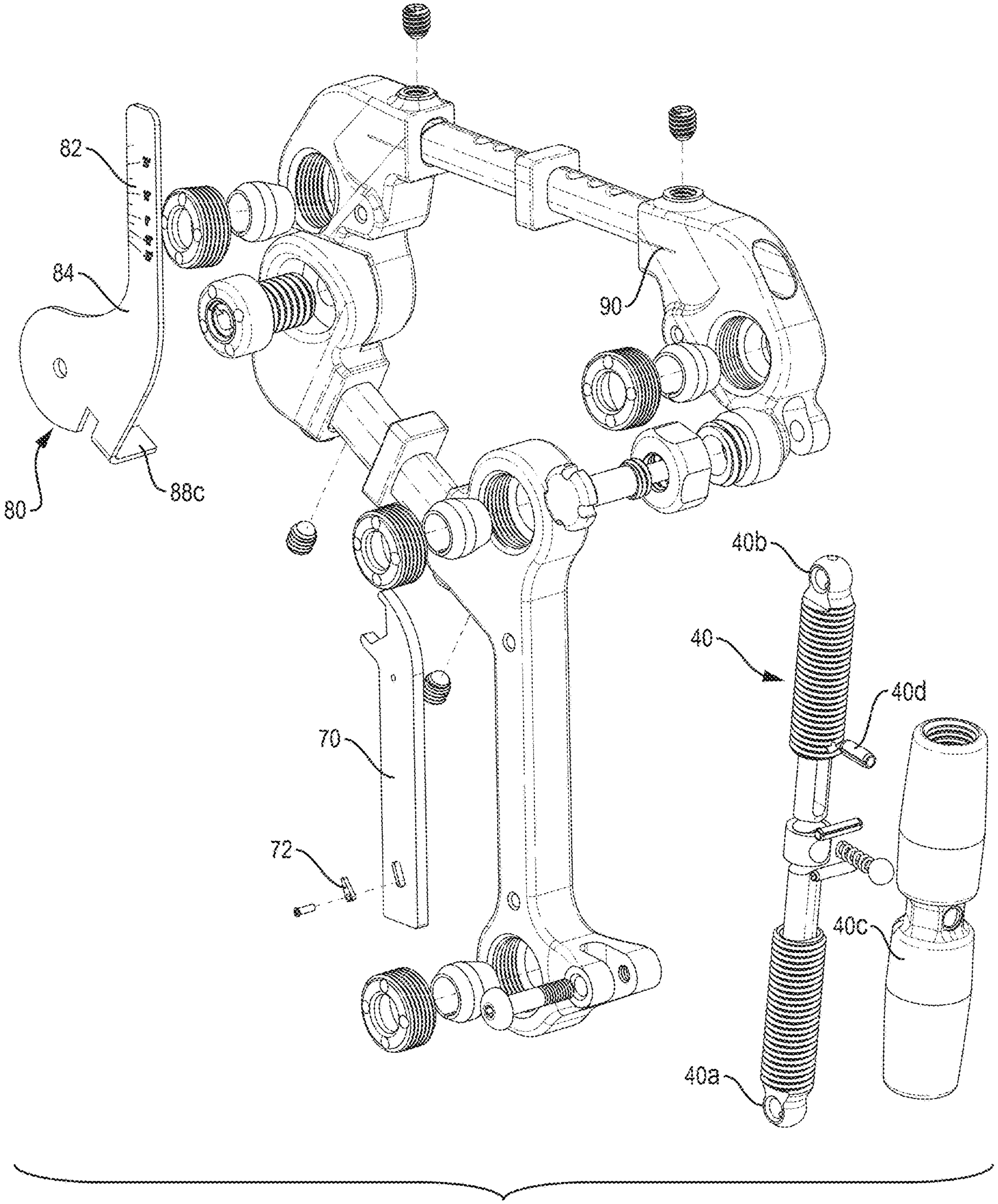
FIG. 4 is an exploded view of the fixator of FIG. 2 showing the fixator assembly with an angle measurement tool, wrench, and additional details of the distraction element assembly.

FIG. 4 is another exploded view of the fixator of FIG. 2 adding the optional angle measurement tool 80 and identifying additional details of the distraction element assembly 40. The angle measurement tool 80 comprises an angle scale arm, and angle scale stop 88*c* that abuts a top side of the arm 24 in operation, and an angle scale 82. The head element 10 has a datum line 90 disposed thereon. In operation, the distraction angle or a change in the distraction angle is measured by reading the angle scale 82 where it crosses the datum line 90.

The distraction element 40 is shown in this figure as an assembly and would be the same as in the fixator of FIG. 1. In FIG. 4, the distraction element assembly 40 comprises a distraction element first threaded part 40*a* and a distraction element second threaded part 40*b*. The second threaded part 40*b* is threaded opposite of the first threaded part 40*a*. The distraction element also comprises distraction element barrel 40*c* with internal threads configured and sized to accept the first and second threaded parts within to adjust an overall length of distraction element assembly 40. The assembly also comprises a pin or screw 40*d* configured to fit in a radial hole in the barrel 40*c* and a recess in the first or second threaded parts 40*a* or 40*c* in order to prohibit rotation of the barrel 40*c* to fix the length of the distraction element assembly 40. The distraction element assembly 40 may also comprise a hexagonal or square shape that is configured to accept an open end wrench 70 for turning the barrel and adjusting the length of the assembly.

Figure 5:
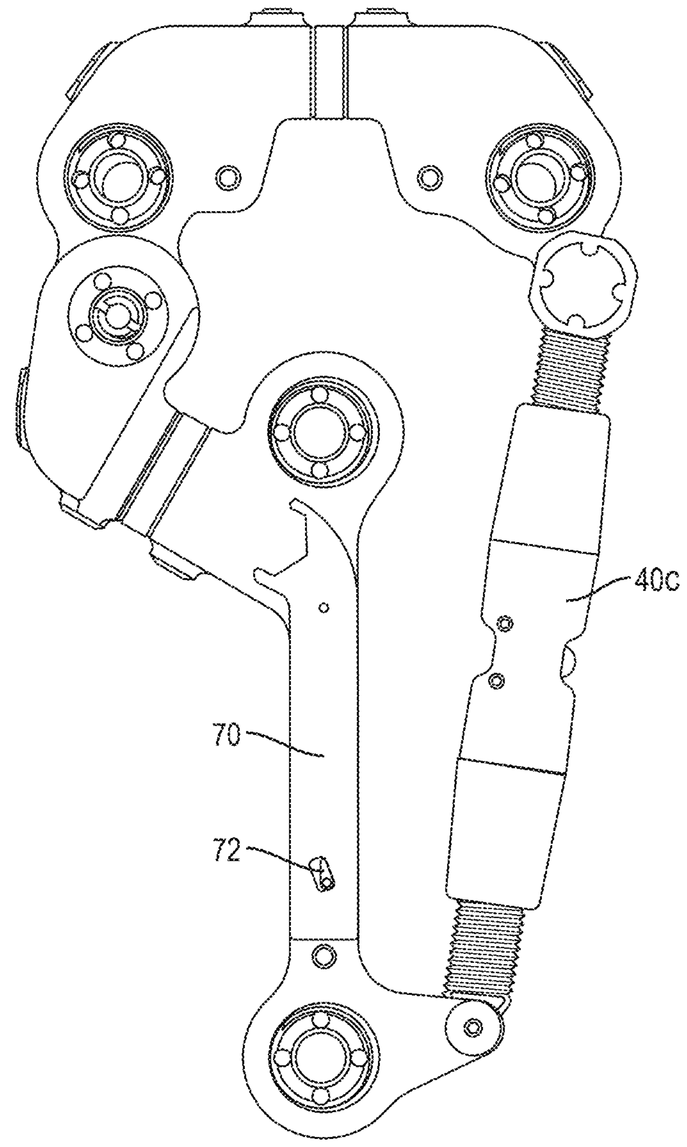
FIG. 5 is a plan view of a fixator according to the present invention showing details of a distraction element wrench attached to the fixator.

FIG. 5 discloses a fixator assembly that further comprises an optional wrench 70. The wrench preferably has the same partial profile as the partial outline of the shaft element 20 for efficient storage and because it is less likely to catch on an article of clothing. The wrench may be secured to the shaft element 20 by a wrench attaching means 72. The wrench attaching means 72 can be a release latch or a magnet. If the wrench is made of 400 series stainless steel, then the wrench is magnetic and can be held in place by a magnet. The wrench opening is sized to fit the hexagonal or square shape of a part of the distraction element barrel 40*c*. In operation, an operator or surgeon may release the wrench from the shaft element using the wrench attaching means. Then the operator or surgeon may adjust a length of the distraction element to a desired length. Note that the operator can be the patient who is wearing the external fixator.

One of the other improvements over the Baumgart reference is the present invention permits a surgeon to be sure that an osteotomy, i.e., bone cut for bone angulation, is complete. The present design permits distraction element second threaded part 40*b* to be temporarily released and moved out of the way from the head element first end 10*a* in a small motion. After checking, the second threaded part 40*b* and head element first end 10*a* can be reconnected.

Figure 6:
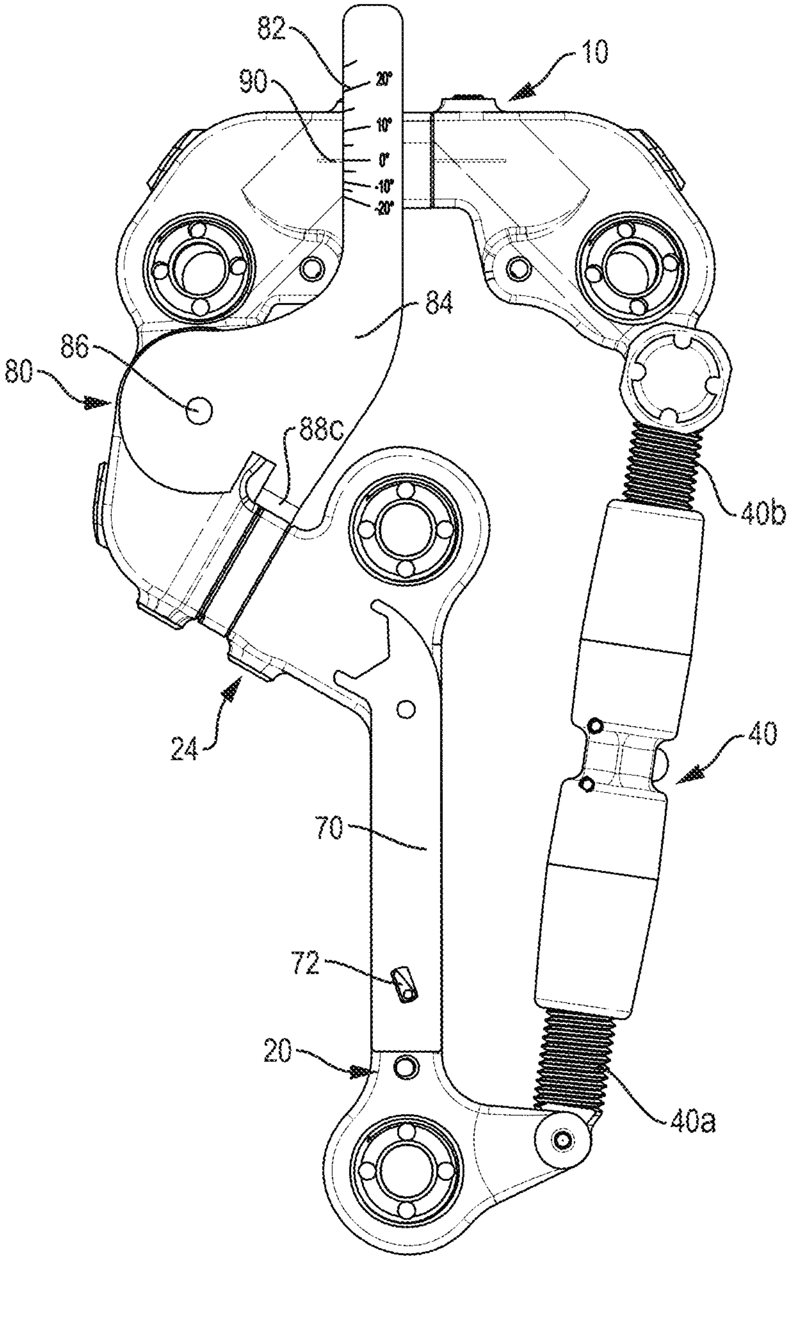
FIG. 6 is a plan view of a fixator according to the present invention showing details of the angle measurement tool.

FIG. 6 is a plan view of the external fixator of the present invention including the wrench 70 and optional angle measurement tool 80. The distraction angle or changes in the distraction angle are determined by reading where the angle scale 82 crosses the datum line 90 on the head element 10. In this view the angle scale stop 88*c* has been stopped against the arm 24. The angle measurement tool 80 is rotatably secured to an angle scale support 86.

The present invention can be provided as a completed assembly, as a collection of parts to be assembled just prior to surgery, or provided as kits that are supplied to hospitals. A kit would include a) a head element first end 10*a, b*) a head element second end 10*b* having a projecting arm 11, c) a plurality of discrete sizes of straight head element sizing inserts 60, d) an elongated shaft element 20 having a shaft element first end 20*a* comprising an elongated arm 24 with an arm second end 24*b, e*) an arm first end 24*a, f*) a plurality of discrete sizes of straight arm sizing inserts 62, and g) a length-adjustable distraction element 40. The there can be five discrete sizes of inserts 60 and 62 in the kit. However, there could be more or fewer than five sizes. The sizes can be extra small, small, medium, large, and extra-large relative to each other. The kit can also include h) a wrench 70 that is sized to adjust a length of the distraction element 40. The wrench could be secured to the shaft element 20 by a wrench attaching means 72. The kit can also include i) an angle measurement tool. A key benefit of such a kit is that a hospital would only have to stock left side and right side fixators, not fixators of many different sizes for both left and right sides. The sizing inserts 60 and 62 would adjust the size of the fixator to fit any patient. This saves a great deal of money by reducing inventory and avoiding running out of a fixator of a particular size.

Figure 7:
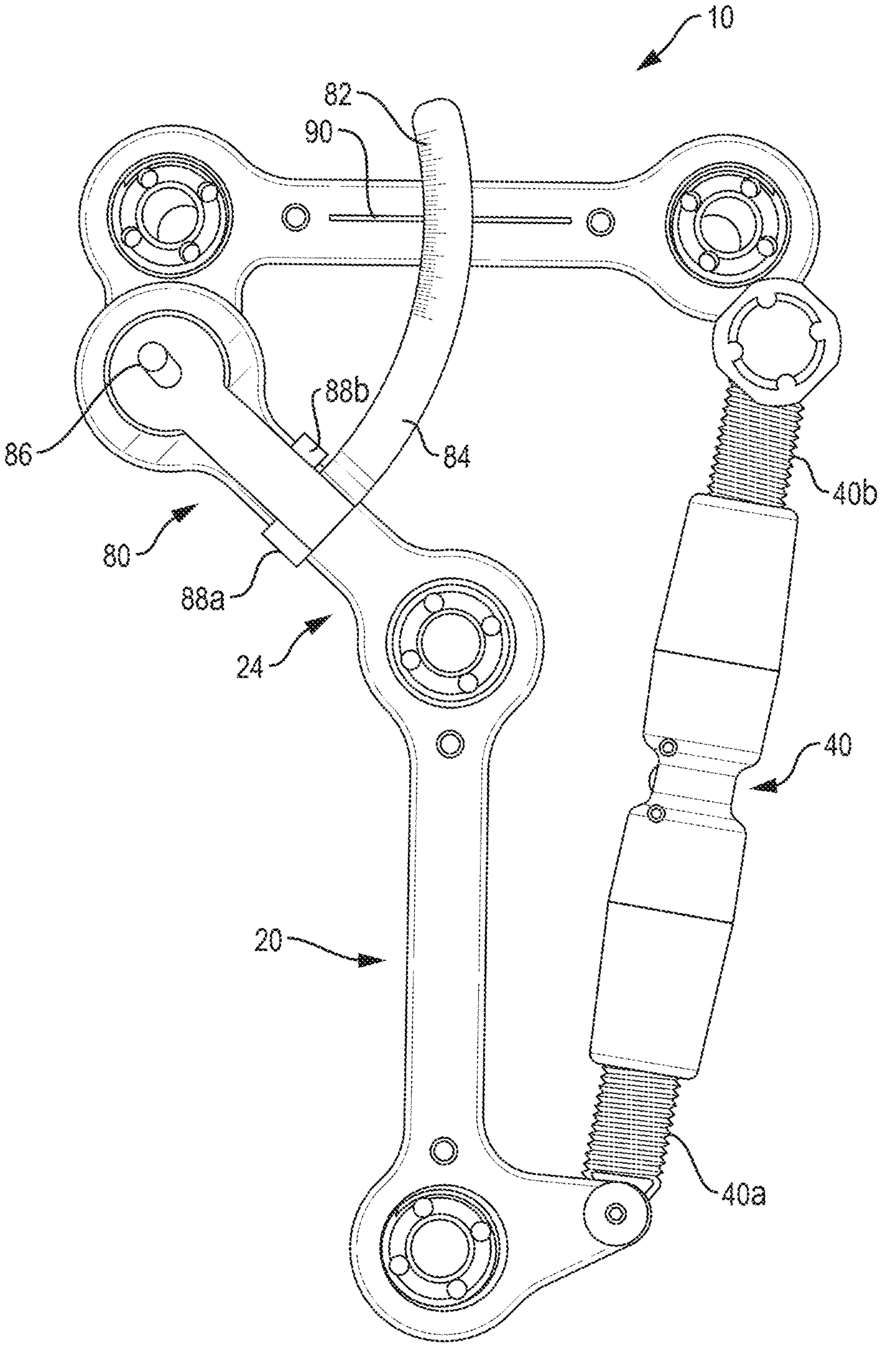
FIG. 7 is a plan view of a version of the angle measurement tool used with a Baumgart fixator.

FIG. 7 discloses a version of the optional angle measurement tool 80 that can be provided for use with another external fixator such as the one described in the Baumgart reference. The angle measurement tool 80 is used to measure an angle or an angle change between the arm 24 and the head element 10. The angle measurement tool comprises an angle scale support 86 rotatably attachable to the arm 24 and an angle scale arm 84 attached at and end of the angle scale support 86. The angle scale arm 84 comprises an angle scale 82 having a plurality of angle gradations thereon. To more precisely read the angle, the head element 10 may have a datum line 90 applied to the head element 10, preferably applied to a longitudinal axis of the head element 10. The precise angle or angle change between the arm 24 and the head element 10 can be read where the scale 82 crosses the datum 90.

The angle scale support 86 can be attached at one end to a guide wire, or can be a guide wire, located at one end of the arm 24. Another end of the angle scale support 86 may have an angle scale first wing 88*a* and an angle scale second wing 88*b* configured to prevent the angle scale support from moving relative to the arm 24.

While there have been described what are at present considered to be the preferred embodiments of this invention, it will be obvious to those skilled in the art that various changes and modifications may be made therein without departing from the invention and it is, therefore, aimed to cover all such changes and modifications as fall within the true spirit and scope of the invention.

The invention claimed is:

1. An external fixator for correcting an angle of a bone comprising:

an elongated head element (10), the head element comprising:

a head element first end (10*a*);

a head element second end (10*b*) installable opposite the head element first end;

a straight head element sizing insert (60) configured to be secured between the head element first end and the head element second end to adjust an overall length of the head element; and a projecting arm (11) extending from the head element second end;

an elongated shaft element (20), the shaft element comprising:
a shaft element first end (20*a*) comprising an elongated arm (24) inclined away from the shaft element first end, the elongated arm comprising:
an arm first end (24*a*) configured to be rotatably attached to the projecting arm; and
an arm second end (24*b*) opposite the arm first end attached to the shaft element first end; and
a straight arm sizing insert (62) configured to be secured between the arm first end and the arm second end;
a shaft element second end (20*b*) opposite the shaft element first end;
a length-adjustable distraction element (40), the distraction element comprising:
a distraction element first threaded part (40*a*) configured to be rotatably attached to the shaft element second end; and
a distraction element second threaded part (40*b*) configured to be rotatably attached to the head element first end and detached from the head element first end to determine whether an osteotomy is complete;
whereby a size of the head element sizing insert (60) and a size of the arm sizing insert (62) is selected to produce a predetermined external fixator configuration that corrects an angle of a bone.

2. The external fixator of claim 1, wherein
the head element sizing insert (60) is a block selected from a plurality of discrete sizes configured to separate the head element first end (10*a*) from the head element second end (10*b*) by a set distance; and
the arm sizing insert (62) is a block selected from a plurality of discrete sizes configured to separate the arm first end (24*a*) from the arm second end (24*b*) by a set distance when assembled.

3. The external fixator of claim 2, wherein the plurality of discrete sizes are extra small, small, medium, large, and extra-large, relative to each other.

4. The external fixator of claim 2, wherein the plurality of discrete sizes of head element sizing inserts (60) result in head element (10) lengths, when assembled, suitable for proximal tibial mediolateral widths between 60 mm and 90 mm.

5. The external fixator of claim 1, the head element sizing insert (60) comprising:
a head element rail (64) configured to be inserted in a respective hole in the head element first end (10*a*) and the head element second end (10*b*), and
respective threaded fasteners (66) configured to secure the head element first end and head element second end at a set distance when assembled.

6. The external fixator of claim 1, the arm sizing insert (62) comprising:
an arm insert rail (68) configured to be inserted in a respective hole in the arm first end (24*a*) and the arm second end (24*b*), and
respective threaded fasteners (66) configured to secure the arm first end and arm second end at a set distance when assembled.

7. The external fixator of claim 1, the distraction element (40) further comprising a distraction element barrel (40*c*) configured to engage the distraction element first threaded part (40*a*) and distraction element second threaded part (40*b*) for adjusting an overall length of the distraction element by rotating the distraction element barrel.

8. The external fixator of claim 7, further comprising:
a wrench (70) configured to be releasably attached to the shaft element (20), the wrench sized to engage and rotate the distraction element barrel (40*c*); and
a wrench attaching means (72) configured to selectively attach and release the wrench from the shaft element, whereby an operator may release the wrench from the shaft element and adjust a length of the distraction element to a desired length.

9. The external fixator of claim 1, further comprising an angle measurement tool (80) configured to measure an angle change between the arm (24) and the head element (10).

10. An external fixator kit that, when assembled, forms an external fixator for correcting an angle of a bone, the kit comprising:
a) a head element (10) first end (10*a*);
b) a head element second end (10*b*) installable opposite the head element first end, the head element second end having a projecting arm (11);
c) a plurality of discrete sizes of straight head element sizing inserts (60) configured to be secured between the head element first end and the head element second end to adjust an overall length of the head element;
d) an elongated shaft element (20), the shaft element comprising a shaft element first end (20*a*), the shaft element first end comprising an elongated arm (24) inclined away from the shaft element first end, the elongated arm comprising an arm second end (24*b*);
e) an arm first end (24*a*);
f) a plurality of discrete sizes of straight arm sizing inserts (62) configured to be secured between the arm first end and the arm second end; and
g) a length-adjustable distraction element (40).

11. The external fixator kit of claim 10, wherein:
the plurality of head element sizing inserts (60) are provided as a plurality of head element sizing insert blocks configured to separate the head element first end (10*a*) from the head element second end (10*b*) by a set distance when assembled; and
the plurality of arm sizing inserts (62) are provided as a plurality of arm sizing insert blocks configured to separate the arm first end (24*a*) from the arm second end (24*b*) by a set distance when assembled.

12. The external fixator kit of claim 10, wherein the plurality of discrete sizes are extra small, small, medium, large, and extra-large, relative to each other.

13. The external fixator kit of claim 10, wherein the plurality of discrete sizes of sizing inserts (60) result in head element (10) lengths, when assembled, suitable for proximal tibial mediolateral widths between 60 mm and 90 mm.

14. The external fixator kit of claim 10, the distraction element (40) comprising:
a distraction element first threaded part (40*a*);
a distraction element second threaded part (40*b*) that is threaded opposite of the first threaded part; and
a distraction element barrel (40*c*) configured to engage the distraction element first threaded part and distraction element second threaded part for adjusting an overall length of the distraction element by rotating the distraction element barrel.

15. The external fixator kit of claim 14, further comprising:
h) a wrench (70) configured to be releasably attached to the shaft element (20), the wrench sized to engage and rotate the distraction element barrel (40*c*); and
the shaft element (20) further comprising a wrench attaching means (72) configured to selectively attach and release the wrench from the shaft element, whereby an operator may remove the wrench from the shaft element and adjust a length of the distraction element to a desired length.

16. The external fixator kit of claim 10, further comprising:

i) an angle measurement tool (80) configured to measure an angle change between the arm (24) and the head element (10).

17. An external fixator kit that, when assembled, forms an external fixator for correcting an angle of a bone, the kit comprising:

a) a head element (10) first end (10*a*);

b) a head element second end (10*b*) installable opposite the head element first end, the head element second end having a projecting arm (11);

c) a straight head element sizing insert (60) comprising:

i) a straight head element rail (64) configured to be inserted in a respective hole in the head element first end (10*a*) and the head element second end (10*b*); and ii) a plurality of threaded fasteners (66) configured to secure the head element first end and head element second end at a set distance when assembled;

d) an elongated shaft element (20), the shaft element comprising a shaft element first end (20*a*), the shaft element first end comprising an elongated arm (24) inclined away from the shaft element first end, the elongated arm comprising an arm second end (24*b*);

e) an arm first end (24*a*);

f) a straight arm sizing insert (62) comprising:

a straight arm insert rail (68) configured to be inserted in a respective hole in the arm first end (24*a*) and the arm second end (24*b*), and another plurality of threaded fasteners (66) configured to secure the arm first end and arm second end at a set distance when assembled; and g) a length-adjustable distraction element (40).

18. The external fixator kit of claim 17, the g) distraction element (40) comprising:

i) a distraction element first threaded part (40*a*);

ii) a distraction element second threaded part (40*b*) that is threaded opposite of the first threaded part; and iii) a distraction element barrel (40*c*) configured to engage the distraction element first threaded part and distraction element second threaded part for adjusting an overall length of the distraction element by rotating the distraction element barrel.

19. The external fixator kit of claim 18, the g) distraction element further comprising:

iv) a pin or screw (40*d*) configured to fit in a radial hole in the barrel (40*c*) and a recess in the first threaded part (40*a*) or second threaded part (40*b*) for prohibiting rotation of the distraction element (40) when assembled.

20. The external fixator kit of claim 17, further comprising:

h) a wrench (70) configured to be releasably attached to the shaft element (20), the wrench sized to engage and rotate the distraction element barrel (40*c*); and the shaft element (20) further comprising a wrench attaching means (72) configured to selectively attach and release the wrench from the shaft element, whereby an operator may remove the wrench from the shaft element and adjust a length of the distraction element to a desired length.

* * * * *